(12) United States Patent
Douroumis (10) Patent No.: US 9,375,399 B2
(45) Date of Patent: Jun. 28, 2016

(54) METHOD OF COATING MICRONEEDLE DEVICES

(71) Applicant: University of Greenwich, London (GB)

(72) Inventor: Dionysios Douroumis, London (GB)

(73) Assignee: University of Greenwich, London (GB)

( * ) Notice: Subject to any disclaimer, the term of this patent is extended or adjusted under 35 U.S.C. 154(b) by 0 days.

(21) Appl. No.: 14/344,964

(22) PCT Filed: Sep. 17, 2012

(86) PCT No.: PCT/GB2012/000727
§ 371 (c)(1),
(2) Date: Mar. 14, 2014

(87) PCT Pub. No.: WO2013/038137
PCT Pub. Date: Mar. 21, 2013

(65) Prior Publication Data
US 2014/0350457 A1 Nov. 27, 2014

(30) Foreign Application Priority Data

Sep. 16, 2011 (GB) .................................. 1116143.7
Feb. 1, 2012 (WO) ................ PCT/GB2012/000104

(51) Int. Cl.
| A61M 5/158 | (2006.01) |
| A61K 9/00 | (2006.01) |
| A61M 37/00 | (2006.01) |
| A61K 47/10 | (2006.01) |
| A61K 47/26 | (2006.01) |
| B05C 5/02 | (2006.01) |

(52) U.S. Cl.
CPC ............... *A61K 9/0021* (2013.01); *A61K 47/10* (2013.01); *A61K 47/26* (2013.01); *A61M 37/0015* (2013.01); *A61M 2037/0046* (2013.01); *A61M 2037/0053* (2013.01); *A61M 2207/00* (2013.01); *B05C 5/0225* (2013.01)

(58) Field of Classification Search
CPC ............ A61K 9/0021; A61M 37/0015; B05C 5/0225
USPC ........................ 427/2.3; 424/449; 604/506, 22
See application file for complete search history.

(56) References Cited

U.S. PATENT DOCUMENTS

| 2004/0096455 | A1* | 5/2004 | Maa ..................... A61B 17/205 424/184.1 |
| 2005/0197308 | A1 | 9/2005 | Dalton et al. |
| 2008/0226687 | A1 | 9/2008 | Cormier et al. |
| 2008/0269666 | A1 | 10/2008 | Wang et al. |
| 2008/0269685 | A1* | 10/2008 | Singh ................... A61K 9/0021 604/173 |
| 2010/0030100 | A1* | 2/2010 | Tokumoto .......... A61B 10/0035 600/556 |
| 2010/0221314 | A1* | 9/2010 | Matsudo et al. .............. 424/449 |

FOREIGN PATENT DOCUMENTS

| EP | 2153863 | 2/2010 |
| JP | 2010131123 | 6/2010 |

(Continued)

*Primary Examiner* — Cachet Sellman
(74) *Attorney, Agent, or Firm* — Cesari and McKenna LLP (57) ABSTRACT

Microneedle devices are spray coated by nozzles which jet dispense dots onto the individual needles of a microneedle device from a spray nozzle which is angled with respect to the plane of the microneedle device. An angle of between 70° and 45° is preferred and can be achieved by providing the microneedle devices on a support which is inclined at 20° to 45° to the horizontal and using a spray nozzle with a vertical axis.

13 Claims, 4 Drawing Sheets

(56) References Cited

FOREIGN PATENT DOCUMENTS

| WO | WO-01/94027 | 3/2001 |
|----|----|----|
| WO | WO-02/07813 | 1/2002 |
| WO | WO-2004/020111 | 3/2004 |
| WO | WO-2006/022933 | 10/2006 |
| WO | WO-2006/138719 | 5/2007 |
| WO | WO-2007059289 | 8/2008 |
| WO | WO-2009/009004 | 1/2009 |
| WO | WO-2009/081122 | 7/2009 |
| WO | WO-2009/081125 | 7/2009 |

* cited by examiner

METHOD OF COATING MICRONEEDLE DEVICES

CROSS-REFERENCE TO RELATED APPLICATIONS

This application is the National Stage of International Application No. PCT/GB2012/000727 filed on Sep. 17, 2012, which claims the benefit of European Application No. 1116143.7 filed on Sep. 16, 2011 and International Application No. PCT/GB2012/000104, filed on Feb. 1, 2012. The contents of each application are hereby incorporated by reference in their entirety.

This invention relates to microneedle devices and in particular to a method of coating microneedle devices and microneedle devices so coated.

Drugs and pharmacological agents including peptides, proteins, vaccines and DNA or RNA are currently delivered almost exclusively by the parenteral route if oral route is not available, due to poor absorption, drug degradation and/or bioavailability. However, parenteral administration encounters several problems where for example hypodermic needles require expertise for delivery, can lead to transmission of blood infections due to needle sticking or intentional needle reuse and cause pain leading to reduced patient compliance.

Transdermal drug delivery has been introduced as an attractive alternative to replace needles because it is relatively easy to use, safe, and painless. However, the tough barrier posed by the skin's outer layer of stratum corneum has limited the applicability of this method to drugs that are hydrophobic, low molecular weight, and potent.

Against this background micron-scale needles assembled on a transdermal patch have been proposed as a hybrid between hypodermic needles and transdermal patches to overcome the individual limitations of both injections and patches. These microneedle devices have proved relatively painless compared to hypodermic needles. In contrast to transdermal patches, microneedle devices have been successfully used to deliver a variety of large and hydrophilic compounds into the skin, including proteins and DNA. The in vitro skin permeability enhancement of two to four orders of magnitude was observed for certain molecules. In vivo delivery has been shown for peptides, such as insulin and desmopressin, genetic material, including plasmid DNA and oligonucleotides and vaccines.

Further details of and references to additional information concerning microneedle devices can be found in WO2006/023814.

As mentioned in WO2006/023814 typical methods of coating microneedles (dip coating and spray coating of the entire microneedle devices) have proved problematic. Generally, these approaches are inefficient and unreliable that can result coating imperfections such as uneven or uncoated layers, coating of the substrate rather than the microneedles and variability in the dose of the active substance. Perhaps most importantly, these methods tend to lead to great losses of the active substance and are generally not commercially viable. WO2006/023814 seeks to provide an improved method of coating microstructures by the dip-coating method, but in order to reduce wastage, rather than dipping the entire microneedle device including both the substrate and the microneedles into the active substance, just the tips of the microneedles are dipped into reservoirs provided in or under a mask.

However, even with this method there is inefficiency with loss of active substance typically at least 30-40% and the process taking a relatively long time and being difficult to set up such that the needles always line up with the appropriate hole in the mask. In addition coating by this method is uneven as multiple dipping is required. An additional disadvantage with dip coating is that the non-uniformity of the coating leads to a bulky shape and this can affect the piercing effectiveness of the needles.

Against this background the present invention provides a method of coating microneedle devices comprising spray coating the individual needles of a microneedle device.

Preferably the method comprises directing at least one spray nozzle towards an individual microneedle and spraying said microneedle.

Preferably the spray coating is carried out by jet dispensing. Jet dispensing is a method used for production line assembly of electronic circuit boards, in particular for dispensing adhesive for use in such assembly. The present inventor has identified that such a method in which tiny dots of adhesive are generated can be used in this different field of technology to coat individual microneedles with active substances. A suitable device for producing such dots is described in U.S. Pat. No. 5,505,777.

Preferably the method comprises positioning a microneedle device comprising a substantially planar substrate with upstanding microneedles relative to the spray nozzle of a spraying device such that the plane of the microneedle device is not at right angles to the axis of the spray nozzle then spraying at least one microneedle. Because of the shape of microneedles—protruding upwards from the surface, the inventor has determined that angling the spray nozzle with respect to the needles improved coating uniformity and minimises loss of the active substance. Also because this coats the side of the needle it does not affect the piercing effectiveness of the needle.

Preferably the method comprises positioning the microneedle device and the spray nozzle such that the angle between the axis of the spray nozzle and the plane of the microneedle device is between 70 and 45 degrees.

Preferably the method of positioning the microneedle device relative to the spray nozzle comprises mounting the microneedle device on a support, the support inclined at 20 to 45 degrees to the horizontal, such that when the axis of the spray nozzle is vertical the plane of the microneedle device is angled at between 70 and 45 degrees.

Alternatively the method comprises adjusting the angle of the spray nozzle so that when the support for the microneedle device is horizontal, the spray nozzle is angled with respect to the upwardly extending microneedles.

Preferably the method comprises formulating a solution comprising an active substance and applying that solution to the individual needles of a microneedle device as described above. The term "active substance" is used to describe drugs and pharmacological agents including peptides, proteins, vaccines and DNA or RNA.

Preferably the method comprises formulating an aqueous solution comprising at least a hydrophilic polymer, a sugar and an active substance and applying that solution to the individual needles of a microneedle device as described above.

Preferably the method produces dots with a diameter of 50-500 μm.

Preferably the method is applied to a microneedle device comprising solid rather than hollow microneedles.

In a second aspect of the invention, there is provided a formulation for jet dispensing onto individual microneedles comprising an active substance, a hydrophilic polymer and a sugar in aqueous solution.

Preferably the hydrophilic polymer is a non-ionic poly (ethylene oxide) polymer (POLYOX™) or a polyvinyl caprolactam-polyvinyl acetate-polyethylene glycol graft copolymer (SOLUPLUS®). Preferably the sugar is trehalose. Most preferably the hydrophilic polymer is POLYOX™ and the sugar is trehalose.

Preferably the active substance is a peptide, a protein, a vaccine, DNA or RNA.

In a third aspect, the invention provides a microneedle device having microneedles coated by one of the methods described above.

An embodiment of the method of the invention is described below as a non-limiting example, with reference to the accompanying drawings, in which:

Figure 1:
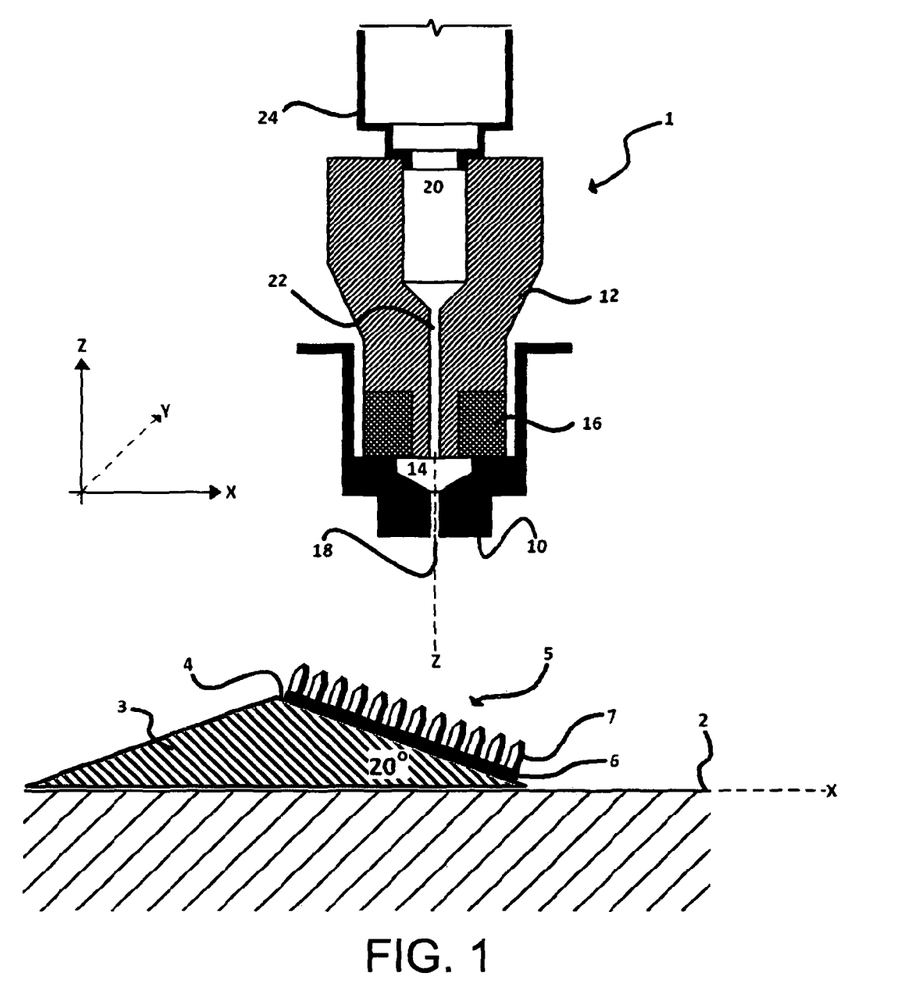
FIG. 1 shows a diagrammatic sectional view of part of the apparatus suitable for carrying out the method of the invention.

FIG. 1 shows a partial view of the viscous material dot generator 1 which is a preferred apparatus for carrying out the method of the invention. A nozzle 10 is rapidly retracted upwardly relative to a fluid feed conduit 12 in order to eject very small droplets or blobs of viscous material at a high velocity from a drop generation chamber 14 inside the nozzle. The nozzle 10 and the fluid feed conduit 12 are both generally cylindrical. The inner diameter of the drop generation chamber 14 is slightly larger then the outer diameter of the fluid feed conduit 12 so that the former can reciprocate relative to the latter. An elastometric cylindrical sealing gasket 16 which surrounds the lower portion of the fluid feed conduit 12 forms a seal between conduit 12 and nozzle 10, while allowing relative reciprocating motion between them. Upward reciprocation of nozzle 10 relative to the lower portion of the fluid feed conduit 12 forces the lower end of the feed conduit 12 into the drop generation chamber 14. The lower end of the fluid feed conduit 12 thus acts as a plunger or generation chamber 14. This forces a minute quantity of viscous fluid from the drop generation chamber 14 through an exit orifice 16 at a high velocity.

The enlarged upper portion of the fluid feed conduit 12 has a chamber 20 which communicates with the drop generation chamber 14 through a narrow feed passage 22. A conventional dispensing syringe 24 has its lower end screwed into the enlarged upper end of the feed conduit 12 so that the interior of the syringe communicates with the chamber 20. A plunger within the syringe 24 is driven by air from a pressurized air reservoir. Pressurized air is selectively metered to the syringe 24 via actuation of a solenoid valve connected to a refill control logic circuit.

The above features are described in U.S. Pat. No. 5,505,777 which gives further details of how the dot generator of the jet dispenser is moved in the X, Y and Z axes to shoot patterns of dots and refers to other patents in order to fully describe the apparatus.

In this embodiment, the dot generator 1 faces a horizontal support 2 on which a mount 3 is positioned. The mount 3 has a top surface 4 which is angled at 20° to the X axis of the horizontal support 2. In use, a microneedle device 5, comprising microneedles 7 upstanding from a substantially planar substrate 6, is placed on the mount 3, such that the Z axis of the nozzle 10 is at an angle of 70° to the plane of the substrate 6 and at 20° to the axis of the upstanding microneedles 7.

The machine is then set up as described in U.S. Pat. No. 5,505,777 to spray individual dots of viscous material from the nozzle 10 onto the individual microneedles 7 of the microneedle device 5. In contrast to the viscous material described in U.S. Pat. No. 5,505,777, rather than spraying adhesive, the viscous material is a drug carrying formulation which dries to deposit a drug on the microneedles 7 of a microneedle device 5. A suitable formulation using a model drug is described in example 1 below.

EXAMPLE 1

A formulation was prepared consisting of 2% w/v POLYOX™ WSR 303 available from Colorcon, 15% w/v Trehalose (a readily available sugar whose chemical name is (2R,3S,4S,5R,6R)-2-(Hydroxymethyl)-6-[(2R,3R,4S,5S,6R)-3,4,5-trihydroxy-6-(hydroxymethyl)oxan-2-yl]oxyoxane-3,4,5-triol), and 0.01% w/v Calcein (a readily available fluorescent dye also known as fluorexon used here as a model drug), with the remainder being water.

All solid components (0.01% w/v calcein, 15% w/v trehalose) were dissolved in deionised water prior to the addition of the polymer. Next POLYOX™ WSR 303 powder was slowly added to the solution in the amount necessary to achieve the desired concentration. The solution was left in a shaker at 50 rpm for 24 h in order to facilitate complete dissolution of the polymer.

The formulation was introduced into a Nordson Asymtek DISPENSEMATE™ 583 jetting device fitted with a DJ9000 nozzle and a microneedle device was placed on a mount having a planar mount surface at 20° to the horizontal, such that with the nozzle vertical it was at 20° to the upwardly extending needles on the device because the plane of the substrate of the microneedle device is at 20° to the horizontal (i.e. 70° to the axis of the nozzle).

The distance between the nozzle and target needle was set at 2.5 mm. Each needle in the array was coated on one side by deposition of three droplets of the formulation dispensed using the jet. An interval of 1 minute was allowed between depositions of multiple droplets for the solution to dry.

The microneedle device used in the example was a solid metal uncoated type obtainable from Professor Mark Prausnitz of Georgia Tech Research Institute and having a total substrate size of 10 mm×15 mm with microneedles 900 μm long and approximately 250 μm wide.

The droplet size was determined as it comes out of the nozzle and when the droplet covers the target surface and table 1 below presents the intra-day variability in the theoretical diameter of the droplet when leaving the nozzle and the actual observed diameter of the dot deposited on the substrate.

Several trials were carried out to reduce the droplet particle size which was found to depend on the formulation composition. The droplet sizes reported below in table 1 are the smallest that could be obtained for the formulation using the particular combination of needle size, diameter of nozzle, fluid pressure and stroke length. These parameters were set at: needle size, 3.2 mm; nozzle diameter, 25 μm unitized with 150 μm seat; fluid pressure, 10 Bar; stroke length, 15 mm.

TABLE 1

| Example 1 | Dot volume (nl) (n = 4) | Theoretical radius (µm) | Theoretical diameter (µm) | Actual diameter on the substrate (µm) |
|---|---|---|---|---|
| 0 h | 3.87 | 97.0 | 194.0 | 350-400 |
| 3 h | 4.16 | 99.7 | 199.4 | |
| 6 h | 3.81 | 96.9 | 193.8 | |
| Average ± SD | 3.95 ± 0.19 | 97.9 ± 1.6 | 195.7 ± 3.2 | |

In order to determine dot volume and theoretical diameter, a total of 4000 dots were dispensed into a 0.2 ml Eppendorf tube. The mass of the dispensed liquid was recorded in order to determine the volume of 1 dot and its theoretical diameter. The intra-day variability in theoretical diameter of the dot was also investigated. In order to determine the amount of the model drug deposited on the microneedle devices, the coating was dissolved off in deionised water and model calcein concentration was measured using UV/Vis spectroscopy.

Figure 2:
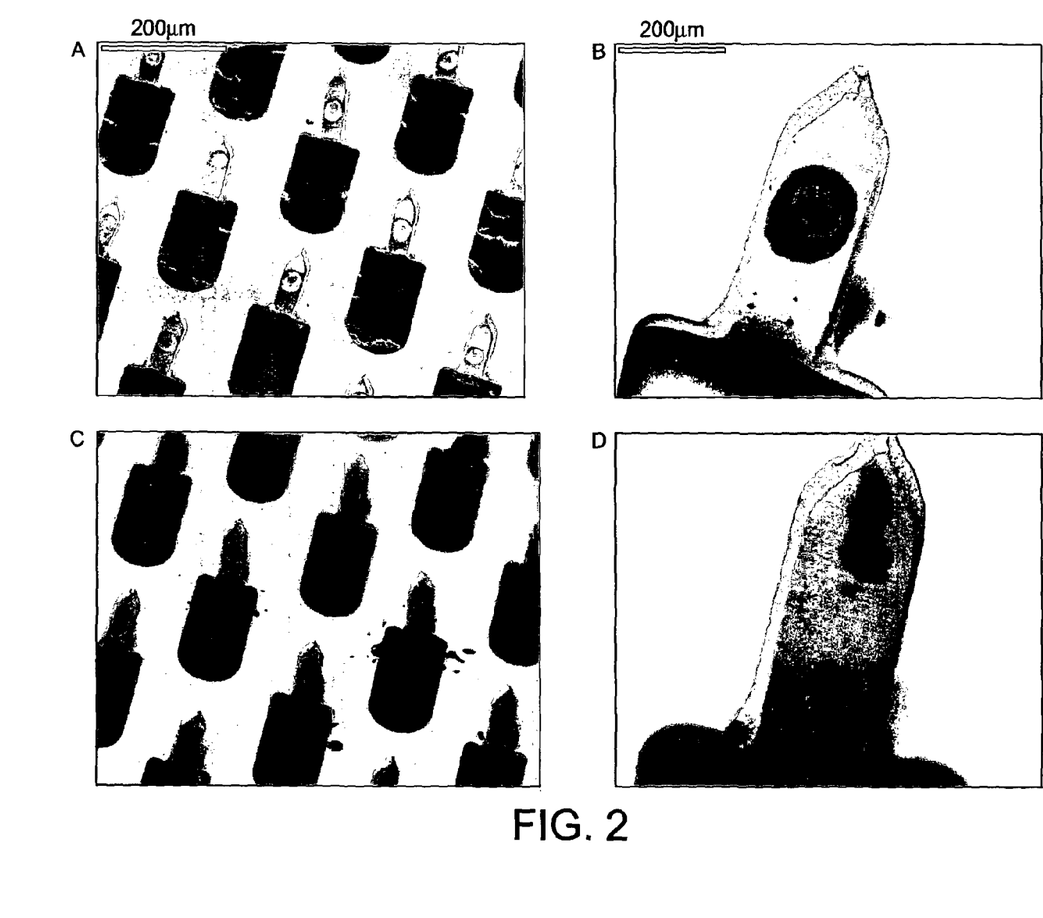
FIGS. 2A-D shows SEM images of a microneedle device coated with three dots of the formulation of example 1.

FIGS. 2A-2D show SEM images of the coated devices; FIGS. 2A and 2B show images of portions of arrays with the dots of coating clearly visible on the microneedles and only a small amount on the substrate. FIG. 2C is an enlarged view of one of the microneedles on the microneedle device of FIG. 2A whereas FIG. 2D is an enlarged view of one microneedle on the microneedle device of FIG. 2A.

It can be seen in particular in FIGS. 2A and 2C that the method can produce uniform circular droplets which are positioned on the microneedles of the microneedle device, not on the substrate.

Table 2 below reports the total amount of calcein coated on the microneedle device and shows that the loss in active material is only 3%, i.e. ten times less loss than is typical in prior art coating techniques.

TABLE 2

| | Total amount of Calcein deposited on MNs (µg) | Control (µg) | Total loss µg | Total loss % |
|---|---|---|---|---|
| Example 1 (1% POLYOX ™, 0.01% calcein) 3 dots per needle | 0.0120 ± 0.001 | 0.01238 ± 0.001 | 0.00038 | 3.07 ± 0.2 |

While example 1 shows a particularly effective coating with very low losses indeed, other formulations have been prepared using an alternative model drug—this time FlNa (Fluorescein Sodium) and while the formulations did not achieve the same low-level of losses, the other benefits of this form of spray coating the individual microneedles of a microneedle device were achieved.

Examples 2-6 were prepared, sprayed with the same parameters and tested in the same manner as example 1. Their formulations are set out below in table 3.

TABLE 3

| Formulation | POLYOX ™ WRS 303 (%) | Trehalose (%) | FlNa (%) | Calcein (%) |
|---|---|---|---|---|
| Example 2 | 1 | 15 | 1.0 | — |
| Example 3 | 1 | 15 | 5.0 | — |
| Example 4 | 2 | 15 | 0.5 | — |

TABLE 3-continued

| Formulation | POLYOX ™ WRS 303 (%) | Trehalose (%) | FlNa (%) | Calcein (%) |
|---|---|---|---|---|
| Example 5 | 2 | 15 | 1.0 | — |
| Example 6 | 2 | 15 | 5.0 | — |

As with example 1, the theoretical and actual dot-sizes were measured with the following results (Table 4).

TABLE 4

| | Dot volume (nl) (n = 4) | Theoretical radius (µm) | Theoretical diameter (µm) | Actual diameter on the substrate (µm) |
|---|---|---|---|---|
| Example 2 | | | | |
| 0 h | 4.80 | 104.6 | 209.2 | 350-450 |
| 5 h | 4.22 | 99.7 | 199.4 | |
| Average ± SD | 4.51 ± 0.41 | 102.2 ± 3.5 | 204.3 ± 6.9 | |
| Example 3 | | | | |
| 0 h | 3.20 | 91.0 | 182.0 | 400-450 |
| 5 h | 2.41 | 83.0 | 166.0 | |
| Average ± SD | 2.81 ± 0.56 | 87.0 ± 5.7 | 174 ± 11.3 | |
| Example 4 | | | | |
| 0 h | 3.89 | 97.58 | 195.16 | 400-450 |
| 6 h | 3.38 | 93.11 | 186.23 | |
| Average ± SD | 3.64 ± 0.36 | 95.3 ± 3.2 | 190.7 ± 6.3 | |
| Example 5 | | | | |
| 0 h | 3.54 | 94.6 | 189.2 | 400-450 |
| 5 h | 3.20 | 91.4 | 182.8 | |
| Average ± SD | 3.37 ± 0.24 | 93.0 ± 2.3 | 186.0 ± 4.5 | |
| Example 6 | | | | |
| 0 h | 3.52 | 94.38 | 188.76 | 400-450 |
| 3 h | 3.68 | 95.79 | 191.58 | |
| Average ± SD | 3.60 ± 0.12 | 95.1 ± 1.0 | 190.2 ± 2.0 | |

The amount of loss was also determined in the same manner as with example 1, and table 5 below reports the results.

TABLE 5

| | Total amount of FlNa deposited on MNs (µg) | Control (µg) | Total loss µg | Total loss % |
|---|---|---|---|---|
| Example 2 (1% POLYOX ™, 1% FlNa) | | | | |
| 3 dots per needle | 1.63 ± 0.47 | 6.19 ± 0.89 | 4.56 ± 0.47 | 73.7 ± 7.6 |
| 1 dot per needle | 0.99 ± 0.15 | 2.28 ± 0.13 | 1.29 ± 0.15 | 56.5 ± 6.5 |
| Example 3 (1% POLYOX ™, 5% FlNa) | | | | |
| 3 dots per needle | 9.30 ± 0.49 | 23.51 ± 3.02 | 14.21 ± 0.49 | 60.4 ± 2.1 |
| 1 dot per needle | 3.35 ± 1.57 | 7.93 ± 1.00 | 4.59 ± 1.57 | 57.8 ± 19.8 |

TABLE 5-continued

| | Total amount of FlNa deposited on MNs (µg) | Control (µg) | Total loss | |
|---|---|---|---|---|
| | | | µg | % |
| Example 4 (2% POLYOX ™, 0.5% FlNa) | | | | |
| 3 dots per needle | 0.71 ± 0.15 | 2.93 ± 0.29 | 2.22 ± 0.15 | 75.6 ± 5.1 |
| 1 dot per needle | 0.37 ± 0.06 | 1.00 ± 0.06 | 0.63 ± 0.06 | 63.1 ± 6.4 |
| Example 5 (2% POLYOX ™, 1% FlNa) | | | | |
| 3 dots per needle | 0.52 ± 0.1 | 6.56 ± 0.62 | 6.05 ± 0.10 | 92.1 ± 1.6 |
| 1 dot per needle | 0.54 ± 0.13 | 2.27 ± 0.16 | 1.65 ± 0.13 | 75.2 ± 6.1 |
| Example 6 (2% POLYOX ™, 5% FlNa) | | | | |
| 3 dots per needle | 8.73 ± 1.55 | 25.56 ± 1.64 | 16.83 ± 1.55 | 65.8 ± 6.1 |
| 1 dot per needle | 2.71 ± 0.55 | 9.97 ± 1.11 | 7.35 ± 0.83 | 73.0 ± 6.0 |

Figure 3:
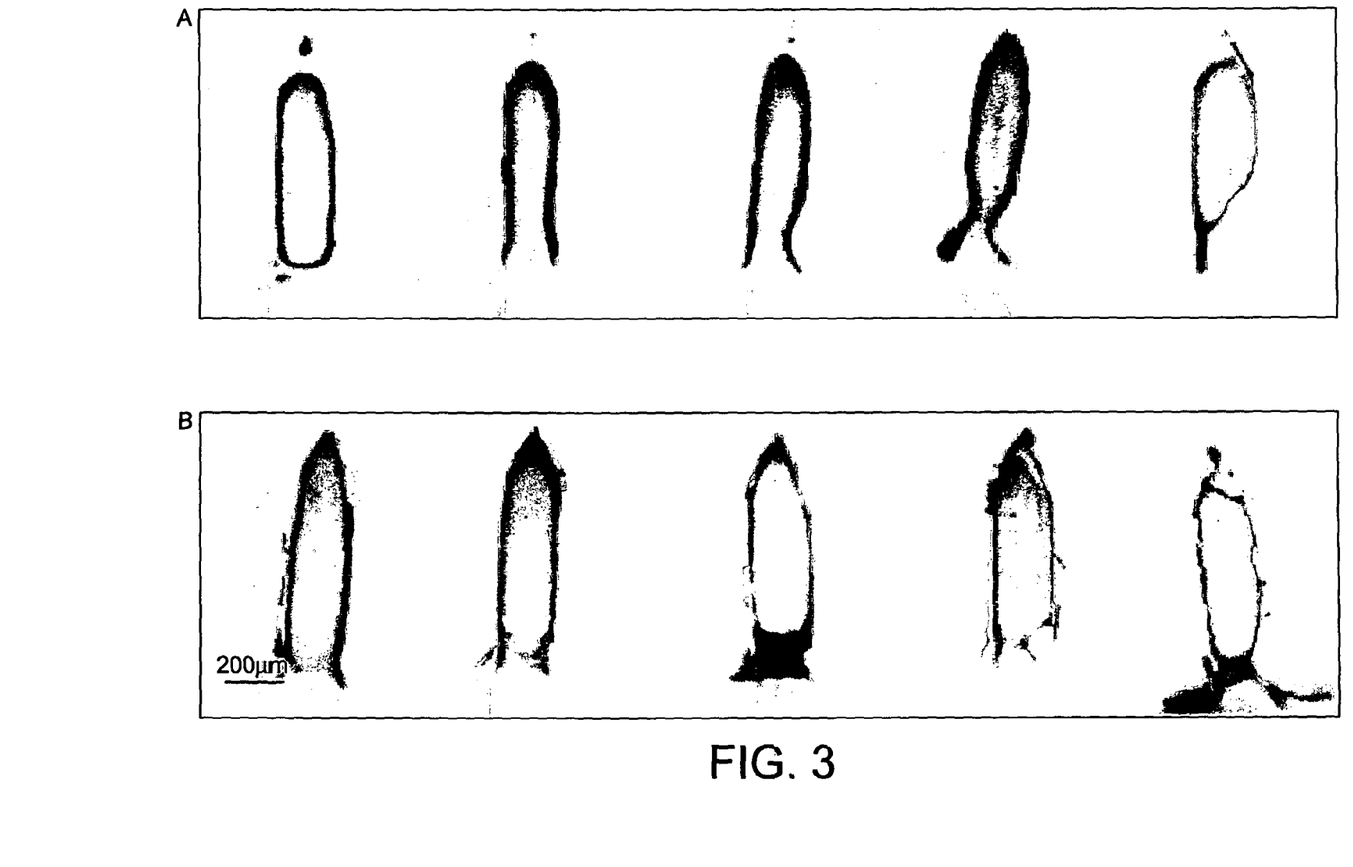
FIGS. 3A and 3B show fluorescence microscopy images of a row of microneedles coated with one dot and three dots respectively of the formulation of example 2.
Figure 4:
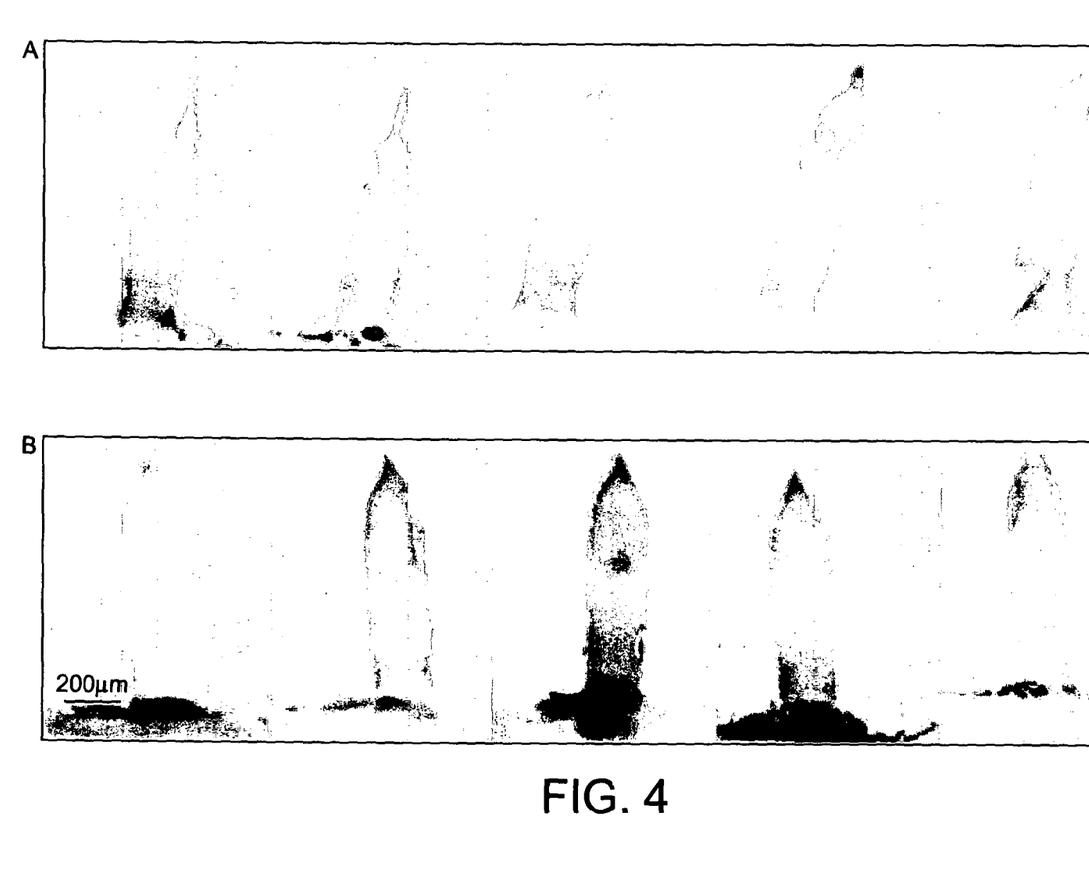
FIGS. 4A and 4B show fluorescence microscopy images of a row of microneedles coated with one dot and three dots respectively of the formulation of example 6.

While it can be seen that the losses are rather higher in these examples than example 1, they all have a greater amount of model drug coated on the needles and the uniformity of coating is superior to known coating methods. FIGS. 3 and 4 show fluorescence microscopy images of the microneedles coated with the formulations of examples 2 and 6 respectively, with FIGS. 3A and 4A showing a coating of one dot per needle and FIGS. 3B and 4B showing a coating of three dots per needle. Slightly more uniform coating was obtained by deposition of three dots in comparison to just one. However, at least in comparing FIGS. 3A and 3B, it can be seen that whereas in FIG. 3A most of the model drug is coated on the shaft of the microneedle, leaving the point sharp, in FIG. 3B more of the dispensed fluid has run down the shaft of the needles onto the substrate of the array; this would correlate with the higher loss when 3 dots were applied.

On the other hand, in FIG. 4A it can be seen that with this formulation even with one dot, some of the model drug ends up on the substrate and in fact there is a lower loss when 3 dots are applied.

Two additional examples (example 7 and example 8) have been carried out using an alternative jetting device, in this case a sub-microliter piezoelectric dispenser, specifically, the NANO PLOTTER™ NP 2.1 manufactured by GeSim and very good results were achieved. In contrast to the above tests, using the Nordson Asymtek device, with the GeSim device the angle of the nozzle to the plane of the microneedle device was set at 45 degrees. Table 6 below shows the composition of the examples and it will be seen that in one example POLYOX™ was replaced with an alternative polymer, SOLUPLUS®.

TABLE 6

| Formulation | POLYOX ™ WRS 303 (%) | Trehalose (%) | FlNa (%) | SOLUPLUS ® (%) |
|---|---|---|---|---|
| Example 7 | 0.2 | 15 | 15 | — |
| Example 8 | — | 15 | 15 | 5.0 |

These experiments also achieved excellent results as shown in table 7 below:

TABLE 7

| | Total amount of FlNa deposited on MNs (µg) | Control (µg) | Total loss | |
|---|---|---|---|---|
| | | | µg | % |
| Example 7 | | | | |
| 3 dots per needle | 4.86 ± 0.41 | 5.01 ± 0.53 | 0.15 | 2.99 |
| 1 dot per needle | 2.32 ± 0.19 | 2.52 ± 0.10 | 0.20 | 7.93 |
| Example 8 | | | | |
| 3 dots per needle | 9.65 ± 0.52 | 10.05 ± 3.02 | 0.40 | 3.98 |
| 1 dot per needle | 4.62 ± 1.57 | 5.03 ± 0.96 | 0.41 | 8.15 |

As can be seen from these examples, losses of less than 10% can be achieved using this method. It will be noted that whereas in the examples using the Nordson Asymtek device the results were better when Calcein was used as a model drug, than when FlNa was used, in the examples using the GeSim device, extremely low levels of losses are achieved despite using FlNa as the model drug.

While the non-limiting examples given above adequately support the entire scope of the invention, the skilled man will appreciate that various alternatives could be made within the ambit of the invention as defined by the claims. For example, while the devices used for spraying the formulations were the Nordson Asymtek DISPENSEJET™, and the GeSim NANO PLOTTER™, alternative devices are available that carry out the same function and carry out "jet dispensing" in a similar fashion.

Likewise, while the examples have used model drugs which allow for easy detection, in use actual drugs would be dispensed onto the microneedles, and while the formulations in the examples used POLYOX™ (or in one case SOLUPLUS®) as a carrier, trehalose to protect the model drug and were based on a aqueous solution, alternative polymers or other carriers could be used and different sugars could be used. The media could conceivably dispense with either the polymer or the sugar entirely and possibly not be aqueous, provided the solution has suitable parameters such as viscosity and drying time to allow it to be sprayed onto individual microneedles in accordance with the claimed method.

Moreover, although in this case the microneedle devices were of the solid metal uncoated type having a total substrate size of 10 mm×15 mm with microneedles 900 µm long and approximately 250 µm wide, other sizes could be dealt with by the same method and other types of microneedle device, such as "pocketed" microneedle devices and special designs with "expanded needle-heads".

The invention claimed is:
1. A method of coating a microneedle device, the method comprising spray coating individual needles of a microneedle device by
    directing at least one spray nozzle towards an individual microneedle,
    positioning the microneedle device and the spray nozzle such that the angle between the axis of the spray nozzle and the plane of the microneedle device is between 70 and 45 degrees, and
    spraying the individual microneedle.
2. A method according to claim 1, wherein the spray coating is carried put by jet dispensing.

3. A method according to claim 1, wherein the microneedle device comprises a substantially planar substrate with upwardly extending microneedles.

4. A method according to claim 3, wherein the positioning step comprises mounting the microneedle device on a support and setting the angle of the spray nozzle such that when the support for the microneedle device is horizontal, the spray nozzle is angled with respect to the upwardly extending microneedles.

5. A method according to claim 1, wherein the positioning step comprises mounting the microneedle device on a support, the support inclined at 20 to 45 degrees to the horizontal, such that when the axis of the spray nozzle is vertical the plane of the microneedle device is angled at between 70 and 45 degrees.

6. A method of coating a microneedle device, comprising applying a solution containing an active substance to a microneedle array in accordance with claim 1.

7. A method of coating a microneedle device according to claim 6, comprising formulating a solution comprising an active substance and applying that solution to the individual needles of a microneedle device.

8. A method according to claim 7, comprising formulating an aqueous solution comprising at least a hydrophilic polymer, a sugar, and an active substance and applying that solution to the individual needles of a microneedle device.

9. A method according to claim 8, wherein the hydrophilic polymer is a non-ionic poly(ethylene oxide) polymer.

10. A method according to claim 8, wherein the sugar is trehalose.

11. A method according to claim 6, wherein the active substance is a peptide, a protein, a vaccine, DNA, or RNA.

12. A method according to claim 1, wherein the method produces dots of active substance with a diameter of 50-500 µm on individual microneedles.

13. A method according to claim 1, wherein the microneedle device comprises solid microneedles.

* * * * *